United States Patent
Misra et al.

(10) Patent No.: US 10,234,559 B2
(45) Date of Patent: Mar. 19, 2019

(54) APPARATUS FOR DETECTING SEA MINES

(71) Applicant: BAE SYSTEMS INFORMATION AND ELECTRONIC SYSTEMS INTEGRATION INC., Nashua, NH (US)

(72) Inventors: Anupam K. Misra, Honolulu, HI (US); Andrew N. Acker, Honolulu, HI (US); Shiv K. Sharma, Honolulu, HI (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 364 days.

(21) Appl. No.: 15/340,732

(22) Filed: Nov. 1, 2016

(65) Prior Publication Data
US 2018/0120432 A1    May 3, 2018

(51) Int. Cl.
| | | |
|---|---|---|
| *G01C 3/08* | (2006.01) | |
| *G01S 17/02* | (2006.01) | |
| *G01S 17/89* | (2006.01) | |
| *G01N 33/22* | (2006.01) | |
| *G01S 17/10* | (2006.01) | |

(Continued)

(52) U.S. Cl.
CPC .......... *G01S 17/023* (2013.01); *G01N 33/227* (2013.01); *G01S 7/4802* (2013.01); *G01S 17/026* (2013.01); *G01S 17/10* (2013.01); *G01S 17/88* (2013.01); *G01S 17/89* (2013.01); *G01V 8/02* (2013.01); *G01N 21/6456* (2013.01); *G01N 21/65* (2013.01); *G01N 2021/4709* (2013.01); *G01N 2021/6463* (2013.01)

(58) Field of Classification Search
CPC ........... G01V 8/02; G01S 17/89; G01S 17/88; G01N 21/64; G01N 21/65

USPC ........................................................ 356/4.01
See application file for complete search history.

(56) References Cited

U.S. PATENT DOCUMENTS

| | | | |
|---|---|---|---|
| 5,450,125 A | 9/1995 | Ulich et al. | |
| 8,024,135 B2 * | 9/2011 | Lee .................... | G01N 21/3504 |
| | | | 356/4.01 |

(Continued)

FOREIGN PATENT DOCUMENTS

CN    105044730    6/2015

OTHER PUBLICATIONS

International Search Report, PCT/US17/58307, dated Jun. 29, 2018, 7 pages.

*Primary Examiner* — Mark Hellner
(74) *Attorney, Agent, or Firm* — Antony P. Ng; Russell Ng PLLC; Scott J. Asmus

(57) ABSTRACT

An apparatus for detecting sea mines is disclosed. The apparatus includes a pulsed laser, a collection optics, a long-pass beam splitter, a short-pass beam splitter, a Laser Imaging, Detection and Ranging (LIDAR) channel imager, a Raman channel imager and a florescence channel imager. After the pulsed laser has sent a laser pulse to an ocean surface, the collection optics collects Rayleigh, Raman and florescence scattering return signals reflected from the ocean surface as a result of the laser pulse laser striking the ocean surface and any objects therein. The long-band beam splitter directs the Rayleigh scattering return signals to the LIDAR channel imager. The short-band beam splitter directs the Raman return signals to the Raman channel imager, and directs the florescence return signals to the florescence channel imager.

16 Claims, 2 Drawing Sheets

(51) Int. Cl.
  *G01S 17/88* (2006.01)
  *G01S 7/48* (2006.01)
  *G01V 8/02* (2006.01)
  *G01N 21/64* (2006.01)
  *G01N 21/65* (2006.01)
  *G01N 21/47* (2006.01)

(56) References Cited

U.S. PATENT DOCUMENTS

2007/0035624 A1  2/2007  Lubard et al.
2010/0072367 A1  3/2010  Meurer
2015/0049326 A1  2/2015  Lundquist \* cited by examiner

APPARATUS FOR DETECTING SEA MINES

TECHNICAL FIELD

The present disclosure relates to mine detection in general, and in particular to an apparatus for detecting maritime mines from air.

BACKGROUND

The current state of the art apparatus for detecting sea mines from air utilizes either a passive multi-spectral electro-optical (EO) system or an active imaging Laser Imaging, Detection and Ranging (LIDAR) system. With passive EO systems, mine-like objects (MLOs) are detected through imaging changes in the water leaving radiance signal, and such systems can only be used in daylight conditions. Active imaging LIDAR systems employ a pulsed laser transmitter source to direct a laser pulse at the ocean. A detector is then utilized to measure the return signals (both time of flight and intensity), and the variation in the return signals with respect to the background are used to detect the presence of MLOs. Unlike passive EO systems, active imaging LIDAR systems can be operated during day time and night time.

Both passive EO and active imaging LIDAR systems have difficulties in detecting sea mines located at or just beneath the ocean surface. In the case of passive EO systems, surface and floating mines can act as spectral reflectors of the down welling solar irradiance, presenting the same spectral signature as glint. In the case of active imaging LIDAR systems, it is generally not possible to separate the large surface reflection (glint) from the signal generated by surface and near surface sea mines. Basically, glint effects can cause a reduction in detection performance against surface and near surface sea mines for both passive EO and active LIDAR systems.

SUMMARY

In accordance with one embodiment of the present disclosure, an apparatus for detecting sea mines includes a pulsed laser, a collection optics, a long-pass beam splitter, a short-pass beam splitter, a Laser Imaging, Detection and Ranging (LIDAR) channel imager, a Raman channel imager and a florescence channel imager. After the pulsed laser has sent a laser pulse to an ocean surface, the collection optics collect Rayleigh, Raman and florescence scattering return signals reflected from the ocean surface as a result of the laser pulse laser striking the ocean surface and any objects therein. The long-band beam splitter directs the Rayleigh scattering return signals to the LIDAR channel imager. The short-band beam splitter directs the Raman return signals to the Raman channel imager, and directs the florescence return signals to the florescence channel imager.

The features and advantages described herein are not all-inclusive and, in particular, many additional features and advantages will be apparent to one of ordinary skill in the art in view of the drawings, specification and claims. Moreover, it should be noted that the language used in the specification has been selected principally for readability and instructional purposes and not to limit the scope of the inventive subject matter.

BRIEF DESCRIPTION OF THE DRAWINGS

The invention itself, as well as its modes of use, further objects, and advantages thereof, will best be understood by reference to the following detailed description of an illustrative embodiment when read in conjunction with the accompanying drawings, wherein.

DETAILED DESCRIPTION

The present disclosure provides an apparatus for detecting sea mines and other objects that are either floating or submerged in water. Specifically, the apparatus uses Raman and fluorescence imaging (RFI) signals to identify sea mines and other objects, such as fish, debris, marine plants and algae, oil spills, marine hazards, humans, etc., through their respective spectral features and time of flight. The apparatus can provide real-time images from which various objects can also be identified through their morphologies. The depth of the objects can be obtained by the intensity of the Raman signal of water above the object and also by Laser Imaging, Detection and Ranging (LIDAR).

Figure 1:
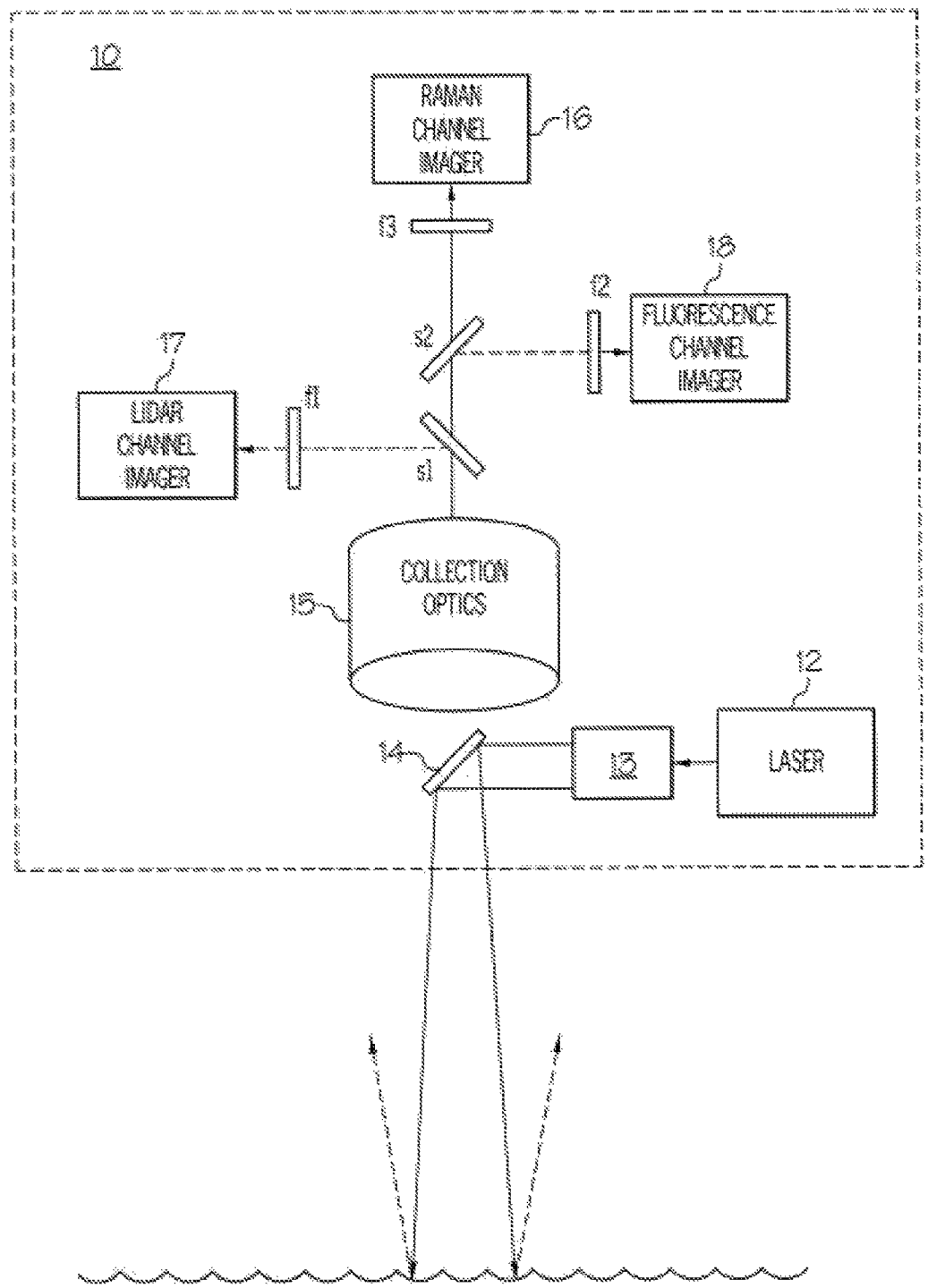
FIG. 1 is a block diagram of an apparatus for detecting sea mines and objects, in accordance with one embodiment of the present disclosure.

Referring now the drawings and in particular to FIG. 1, there is illustrated a block diagram of an apparatus for detecting sea mines and objects, in accordance with one embodiment of the present disclosure. As shown, a RFI-LIDAR system 10 includes a pulsed laser 12, a beam expander 13 and a folding mirror 14 for sending pulsed laser beams. RFI-LIDAR system 10 also includes a collection optics 15 along with a long-pass beam splitter s1 and a short-pass beam splitter s2 for partitioning the return signals by wavelength and for transmitting the appropriate wavelength bands to the Raman channel imager 16, a LIDAR channel imager 17 and a florescence channel imager 18, accordingly.

Pulsed laser 12 can emit a group of high-power pulsed laser beams at an area of ocean surface via beam expander 13 and folding mirror 14. The pulsed laser beam is preferably at a blue-green ocean water penetrating wavelength $\lambda_{laser}$ for a duration $\tau_{laser}$, where $\lambda_{laser}$ is 532 nanometers (nm) and $\tau_{laser}$ is approximately 10 nanoseconds (ns), for example. In the ocean water, wavelengths in the blue-green region, such as 532 nm, have the most depth penetration and useful for sea mine detection. The incident laser beam at the ocean surface can generate a Rayleigh scattering return, a Raman scattering return and possibly a fluorescence scattering return.

The Rayleigh scattering return is the result from a direct reflection of the incident pulsed laser beam off the ocean surface and subsurface objects as well as from the ocean surface itself (glint). At an incident wavelength $\lambda_{as}$, the Rayleigh scattering return from the water is the result from the scattering within the ocean water volume itself.

The Raman scattering return increases with the volume of ocean water illuminated by the incident pulsed laser beam. The Raman scattering return from the water is at a wave number shift of 3,000 to 3,700 cm$^{-1}$ (which corresponds to a wavelength range of 633-662 nm for $\lambda_{laser}$=532 nm).

The fluorescence scattering return is generated by any fluorescent materials at or near the ocean surface, which include algae, seaweed and oil slicks. The fluorescence scattering return signals from the water are at wavelengths greater than $\lambda_{laser}$. The fluorescence wavelength band generally overlaps and extends beyond the Raman wavelength band.

Many types of lasers can be utilized to generate laser beams that result in Rayleigh, Raman and fluorescence scattering returns. For example, UV lasers would be eye safe and the detection operation can be conducted without causing any alarm.

The various scattering return signals from the ocean are collected by collection optics 15 having a camera lenses or telescope. The output of collection optics 15 is sent to long-pass beam splitter s1 having a cutoff wavelength $\lambda_{cutoff_{13}\_s1}$ greater than $\lambda_{laser}$ but less than the low end of the Raman wavelength band ($\lambda_{cutoff\_s1}$ is between 532 nm and 633 nm for $\lambda_{laser}$=532 nm). Long-pass beam splitter s1 separates the Rayleigh scattering return signals from the Raman and florescence return signals, and directs the Rayleigh scattering return signals to LIDAR channel imager 17 via a bandpass filter f1.

Bandpass filter f1 is a narrow width bandpass filter centered at the laser transmitter wavelength $\lambda_{laser}$. Bandpass filter f1 serves primarily as a solar rejection filter to assure that nearly all the return signals entering LIDAR channel imager 17 are actually Rayleigh scattered return signals caused by the pulsed laser beam from pulsed laser 12. LIDAR channel imager 17 is preferably a range gated intensified charged coupled device (CCD) two-dimensional imaging camera. The camera gating can be adjusted so that it exposes for a time interval $\Delta t_L$ beginning at a delay time $t_{dL}$ after a laser pulse has been emitted from pulsed laser 12, causing the camera to expose from time $t_{dL}$ to $t_{dL}+\Delta_{tL}$. The values $t_{dL}$ and $\Delta_{tL}$ are selected such that LIDAR channel imager 17 only observes Rayleigh scattering return signals that occur at a specific range interval from LIDAR channel imager 17, i.e., from 1 meter to 5 meters below the ocean surface.

Collected light with wavelength greater than $\lambda_{cutoff\_s1}$ is transmitted by long-pass beam splitter s1 to short-pass beam splitter s2. Short-pass beam splitter s2 has a cutoff wavelength $\lambda_{cutoff\_s2}$ that is immediately above the high end of the Raman wavelength band ($\lambda_{cutoff\_s2}$ is 662 nm for $\lambda_{laser}$=532 nm). Short-pass beam splitter s2 separates the Raman return signals and florescence return signals, and directs the florescence return signals to high-pass filter f2 and the Raman return signals to bandpass filter f3.

Bandpass filter f3 is utilized to assure that only return signals in the Raman band wavelengths are passed to Raman channel imager 16. Bandpass filter f3 rejects any return signals at wavelengths between $\lambda_{laser}$ and the low end of the Raman wavelength band (i.e., between 532 nm and 633 nm for $\lambda_{laser}$=532 nm) that pass through long-pass beam splitter s2. In one embodiment, Raman channel imager 16 is a gated, intensified CCD two-dimensional imaging camera, which is gated to only expose during the time interval $t_{dR}$ to $t_{dR}+\Delta_{tR}$. Here, the time gating capabilities of the camera are used to limit the reflected sunlight signal entering Raman channel imager 16. The bulk of the Raman return signals are generated from the upper portion of the ocean water column, for $\lambda_{laser}$=532 nm nearly the entire signal is generated by scattering within the first five meters of the ocean water column. Thus, for $\lambda_{laser}$=532 nm, Raman imager gating parameters $t_{dR}$ and $\Delta_{tR}$ should be adjusted to receive Raman scattering return signals from the ocean surface to approximately five meters below the ocean surface.

High-pass filter f2 is utilized to assure that return signals with wavelengths above the high end of the Raman wavelength band (i.e., 662 nm for $\lambda_{laser}$=532 nm) only are passed to florescence channel imager 18. Like Raman channel imager 16 and LIDAR channel imager 17, florescence channel imager 18 is a gated, intensified CCD two-dimensional imaging camera, for example. Florescence channel imager 18 is gated to only expose during the time interval $t_{df}$ to $t_{df}+\Delta_{tf}$, where the time gating is used to limit the amount reflected sunlight entering florescence channel imager 18. The bulk of the florescence return signals comes from the ocean surface to the first few meters (for wavelengths≥662 nm, the majority of the signal originates from depths less than about 3-5 meters. Unlike Rayleigh scattering and Raman scattering return signals; however, the fluorescence scattering return signals cannot be taken to be an instantaneous process; maximum fluorescence lifetimes for the object of interest can approach 100 ns. For florescence channel imager 18, the exposer duration $\Delta tf$ should be set to correspond to this maximum florescence lifetime (~100 ns), and the exposure start time $t_{df}$ should be set to correspond the round trip time of flight from RFI-LIDAR system 10 to the ocean surface.

A complete RFI-LIDAR image set includes an image from each of Raman channel imager 16, LIDAR channel imager 17, and fluorescence channel imager 18. Each of the images is generated from the same laser pulse, and the images are then simultaneously co-registered. The LIDAR channel images objects in the water column by detecting the Rayleigh scattering return at a depth interval specified by the gating parameters $t_{dL}$ and $\Delta_{tL}$. Both the Raman and fluorescence channel images provide information on the ocean surface and near surface regions of the water column; both channel block returns at the transmitter wavelength $\lambda_{laser}$. The Raman and fluorescence channel are therefore insensitive to the large glint return that can be problematic for LIDAR images of the ocean surface. The RFI-LIDAR image set generated by RFI-LIDAR system 10 provides simultaneous information on the ocean sub-surface, near surface and surface environments by detecting the return signals from three distinct scattering mechanisms (i.e., Rayleigh, Raman and florescence scattering), all induced by the same laser pulse transmitted from pulsed laser 12.

Figure 2:
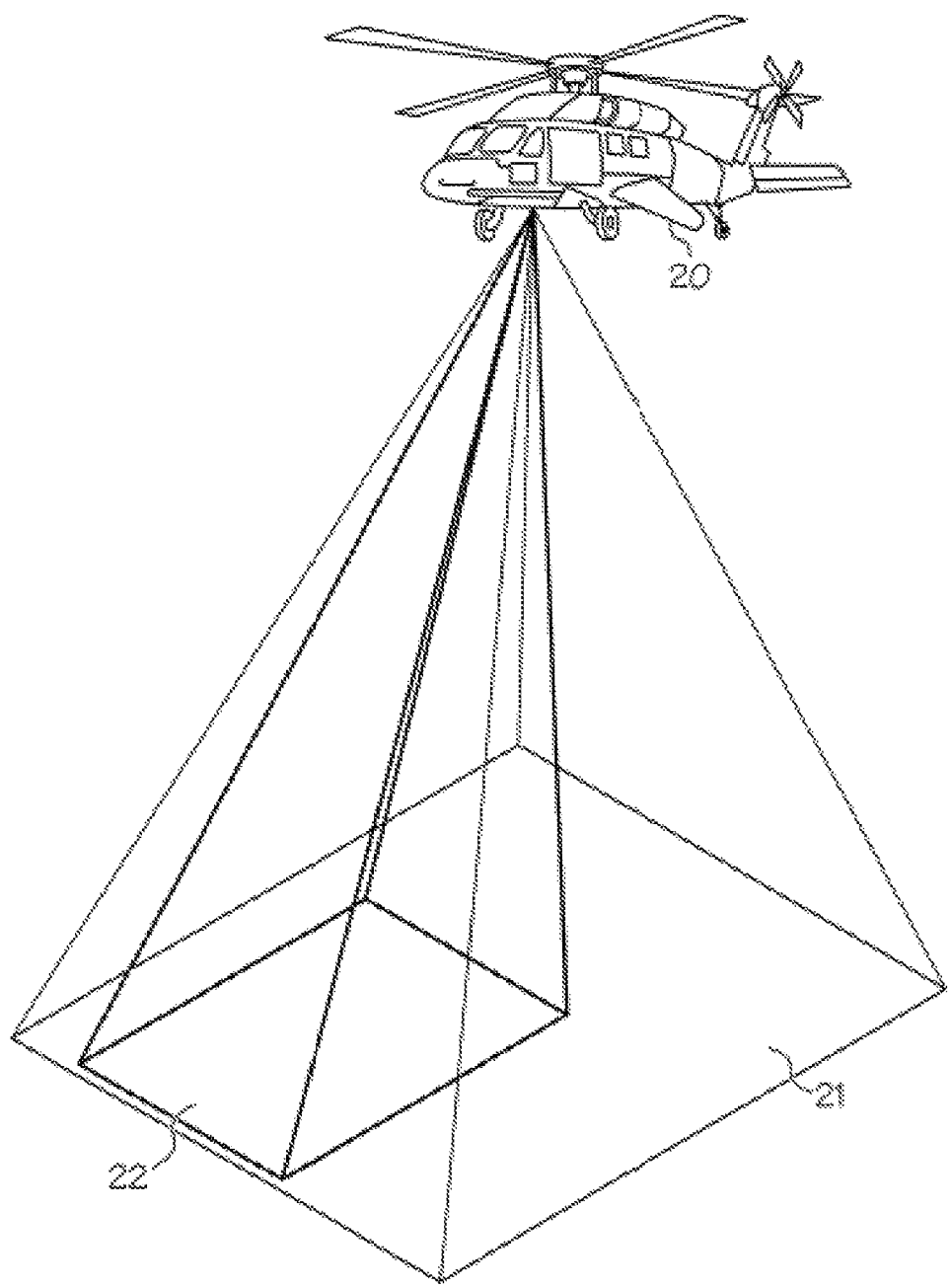
FIG. 2 is a diagram of the apparatus from FIG. 1 being in operation.

With reference now to FIG. 2, there is depicted RFI-LIDAR system 10 from FIG. 1 being in operation. As shown, RFI-LIDAR system 10 can be mounted on a helicopter 20 that can move relative to the ocean surface during operation. RFI-LIDAR system 10 can adjust pulsed laser 12 to use a wide divergence setting that can act as a search mode for scanning a larger area 21. RFI-LIDAR system 10 can also adjust pulsed laser 12 to use a narrow divergence setting that can act as a target verification mode for scanning a smaller area 22. Candidate targets are generated by the LIDAR detector, and these candidates queue the RFI component, which images the target location and segregates target detections from glint false alarms. RFI-LIDAR system 10 can provide the large area coverage available in a LIDAR system with the high detection performance against surface/near surface targets available with a RFI system while leveraging pulsed laser 12 as a single common transmitter.

Although RFI-LIDAR system 10 is shown to be mounted on a helicopter in FIG. 2, it is understood by those skilled in the art that RFI-LIDAR system 10 can also be mounted on other types of aircraft and air vehicles such as unmanned aerial vehicles air ships, and blimp. As an example, RFI-LIDAR system 10 is attached to a ship or barge, which may include an extension, and used to scan the nearby surface for objects, hazards and mines. As another example, RFI-LIDAR system 10 is mounted to a fixed object such as a buoy or in a canal that can scan the water as it passes the fixed object.

The detection of objects in the ocean can be made by looking at the water Raman signal (in the Raman channel) and estimating the amount of water depth the laser has penetrated before hitting the object. For example, if there is a floating object at the surface of water in the ocean, the water Raman signal will become very small, showing only few millimeters of depth due to wetting of the object. The significant drop in the water Raman signal relative to the background will indicate the presence of a floating object in real time; the morphology of this low Raman signal region will characterize the size and shape of the floating object. Similarly, submerged objects that are near the ocean surface can be detected by the sudden change in the water Raman signal. The depth of the object can be estimated from the intensity of the water Raman signal.

The fluorescence channel provides a separate modality for detecting objects at or near the ocean surface while at the same time providing interpretation for the observed signal in the Raman channel. The laser pulse will induce a fluorescence scattering return from fluorescent objects located at or near the ocean surface, and this fluorescence scattering return can generate a signal in both the Raman and fluorescence channels. The observation of a uniform signal in the Raman channel, and no signal in the fluorescence channel indicates the presence of un-occluded sea water. The observation low Raman signal region in a uniform background and no signal in the fluorescence channel indicate the presence of a non-fluorescent object at or near the ocean surface. Finally, the observation of a signal in both the Raman and fluorescence channels indicated of the presence of a fluorescent object at or near the surface. The fluorescence signal can be utilized to detect and map a wide variety floating objects such as algae, marine life, and oil slicks as well as biofouled debris.

The Raman and fluorescence channels also support analysis and interpretation of the imaging LIDAR channel. This is made possible by the fact that the RFI-LIDAR system of the present disclosure generates a full image data set (Raman channel, fluorescence channel, and LIDAR channel images) generated from the same laser pulse. The resulting images are simultaneous and can be tightly co-registered. In the case where the LIDAR channel gate timing is configured such that the LIDAR system images a sub-surface depth interval, the Raman and fluorescence images provide a simultaneous look at the sea surface environment directly above. These data can be utilized to identify presence of surface objects that may affect or occlude the subsurface LIDAR image. With the above-mentioned configuration, the RFI-LIDAR system of the present invention can simultaneously probe the ocean surface, near ocean surface, and sub surface regime for the presence of sea mines and other objects of interest.

The following examples illustrate the sea mine (or object) detection improvements by using RFI-LIDAR system 10. In the first example, LIDAR channel imager 17 of RFI-LIDAR system 10 is configured to image the Rayleigh scattering return from a surface and near-surface depth interval. The generated LIDAR channel image should contain a large localized signal. The interpretation of the LIDAR channel image alone is ambiguous because the return signals could arise from ocean surface glint, ocean surface or near-surface sea mine or a non-mine floating object. Image data from the Raman and fluorescence channels of RFI-LIDAR system 10 can resolve the above-mentioned ambiguity as follows:

(1) The Raman channel image shows a uniform return signal, the fluorescence channel shows no signal above the background noise level, i.e., a bright spot in the LIDAR image;

no spot in the Raman image; and no spot in the fluorescence image.

These results indicate that no surface or near-surface object is present. The signal in the LIDAR channel is most likely due to surface glint and not a sea mine (or other target of interests).

(2) The Raman channel image shows a localized region of sharp signal reduction at an image location corresponding to the large signal in the LIDAR image, the fluorescence channel image shows no signal above the background noise level, i.e., bright spot in the LIDAR image;

very dark spot in the Raman image; and no spot in the fluorescence image.

These results indicate the presence of a non-fluorescent surface object; shape and size analysis of the localized feature in the Raman channel image can be employed to determine if the surface object mine-like or non mine-like.

(3) Same observation as (2) with the exception that the localized Raman signal region only shows a moderate reduction in signal strength relative to the background, i.e., a bright spot in the LIDAR image;

a slightly dark spot in the Raman image; and no spot in the fluorescence image.

These results indicate the presence of a non-fluorescent near surface object; the depth of the object can be estimated by analysis the reduction in the Raman signal level over the object relative to the background. Again, shape and size analysis of the localized feature in Raman channel image can be employed to determine if the near surface object is mine-like or non-mine-like.

(4) The fluorescence channel image shows a localized region of sharp signal increase at an image location corresponding to the large signal in the LIDAR image, the Raman channel image shows a corresponding region sharp signal increase in the same region, i.e., a bright spot in the LIDAR image;

a bright spot in the Raman image; and a bright spot in the fluorescence image.

These results indicate the presence of a fluorescent surface object; shape and size analysis of the localized feature in fluorescence channel image can be employed to determine if the surface object is mine-like or non mine-like. The fluorescence channel image can also show the presence of features such as oil slicks and algae patches which do not generate a detectable signal in the LIDAR channel.

LIDAR channel imager 17 of RFI-LIDAR system 10 can also be configured to image the Rayleigh scattering return from a sub-surface depth interval, and excludes the return from the surface level. In this mode of operation, the sub-surface depth interval is interrogated by the LIDAR channel while, simultaneously, the surface and near-surface layers are interrogated by the Raman and fluorescence channels. Sample results from this configuration are interpreted as follows:

(1) The LIDAR channel shows a localized region of signal level change relative to the background and no corresponding signal in either the Raman and fluorescence channels, i.e., a bright spot in the LIDAR image;

no spot in the Raman image; and no spot in the fluorescence image.

These results indicate the presence of a sub-surface object with no correlated surface signal or surface objects. Shape and size analysis of the localized feature in the LIDAR channel image can be employed to determine if the subsurface object is mine-like or non mine-like.

(2) The LIDAR channel shows no localized signal, the fluorescence and/or Raman channels show a localized signal (as described in cases (2), (3) or (4) of the previous example), i.e.,
- no bright or dark spot in the LIDAR image;
- a spot in the Raman image; and/or
- a bright spot in the fluorescence image.

These results indicate the presence of a surface near surface object, and no correlated subsurface signal. Shape and size analysis of the localized feature can be employed to determine if the surface objects is mine-like or non mine-like.

(3) The LIDAR channel shows a localized region of decreased signal with a corresponding signal in either the fluorescence and/or Raman channels, i.e.,
- a dark spot in the LIDAR image;
- a spot in the Raman image; and/or
- a bright spot in the fluorescence image.

These results indicate the presence of a surface object, the signal in the LIDAR channel is most likely the result of the shadow cast by the surface object.

As has been described, the present disclosure provides an apparatus and method for detecting objects such as sea mines. The RFI-LIDAR system of the present disclosure can simultaneously search both the sub-surface and surface depth intervals for sea mines and other objects of interest. Note importantly that additional capability provided by the Raman and fluorescence imaging channels does not require the portioning or otherwise weakening of the Rayleigh scattering return signal available to the LIDAR channel. The RFI-LIDAR system of the present disclosure can provide an improved probability of detection and decreased probability of false alarms when detecting sea mine targets and other navigation hazards.

While the invention has been particularly shown and described with reference to a preferred embodiment, it will be understood by those skilled in the art that various changes in form and detail may be made therein without departing from the spirit and scope of the invention.

What is claimed is:

1. An apparatus for detecting sea objects, said apparatus comprising:
   - a laser for directing a laser pulse towards an ocean surface;
   - a collection optics for collecting Rayleigh, Raman and florescence scattering return signals caused by said laser pulse striking said ocean surface and said objects therein;
   - a Laser Imaging, Detection and Ranging (LIDAR) channel imager;
   - a Raman channel imager;
   - a florescence channel imager;
   - a long-pass beam splitter for directing said Rayleigh scattering return signals to said LIDAR channel imager; and
   - a short-pass beam splitter for directing said Raman scattering return signals to said Raman channel imager, and for directing said florescence scattering return signals to said florescence channel imager.

2. The apparatus of claim 1, wherein said apparatus further includes a beam expander coupled to said laser.

3. The apparatus of claim 2, wherein said apparatus includes a folding mirror coupled to said beam expander.

4. The apparatus of claim 1, wherein said long-pass beam splitter has a cutoff wavelength $\lambda_{cutoff\_s1}$ greater than a wavelength $\lambda_{laser}$ of said laser, but less than the low end of a Raman wavelength band.

5. The apparatus of claim 1, wherein said short-pass beam splitter has a cutoff wavelength $\lambda_{cutoff\_s2}$ immediately above the high end of a Raman wavelength band.

6. The apparatus of claim 1, wherein said apparatus further includes a first bandpass filter coupled to said LIDAR channel imager, wherein said first bandpass filter has its bandwidth centered at a wavelength $\lambda_{laser}$ of said laser.

7. The apparatus of claim 1, wherein said apparatus further includes a second bandpass filter coupled to said Raman channel imager, wherein said second bandpass filter rejects any return signals at wavelengths between $\lambda_{laser}$ and the low end of a Raman wavelength band.

8. The apparatus of claim 1, wherein said apparatus further includes a high-pass filter coupled to said fluorescence channel imager, wherein said high-pass filter is configured to assure that only return signals having wavelengths above the high end of a Raman wavelength band are passed to said florescence channel imager.

9. The apparatus of claim 1, wherein said LIDAR channel imager is a two-dimensional imaging camera set to expose for a time interval $\Delta t_L$ beginning at a delay time $t_{dL}$ after said laser pulse has been emitted from said laser, causing said camera to expose from time $t_{dL}$ to $t_{dL}+\Delta_{tL}$.

10. The apparatus of claim 9, wherein said delay times $t_{dL}$ and $\Delta_{tL}$ are selected such that said LIDAR channel imager only observes Rayleigh scattering return signals that occur at a specific range interval from said LIDAR channel imager.

11. The apparatus of claim 1, wherein said Raman channel imager is a two-dimensional imaging camera set to only expose during the time interval $t_{dR}$ to $t_{dR}+\Delta_{tR}$, wherein said $t_{dL}$ is a delay time after said laser pulse has been emitted from said laser.

12. The apparatus of claim 1, wherein said florescence channel imager is a two-dimensional imaging camera set to only expose during the time interval $t_{df}$ to $t_{df}+\Delta_{tf}$ in order to limit the amount reflected sunlight entering said florescence channel imager.

13. A method for detecting sea objects, said method comprising:
   - sending a set of laser pulses towards an ocean surface;
   - collecting Rayleigh, Raman and florescence scattering return signals caused by said laser pulses striking said ocean surface and any objects therein;
   - directing and Rayleigh scattering return signals to a Laser Imaging, Detection and Ranging (LIDAR) channel imager;
   - directing said Raman scattering return signals to a Raman channel imager;
   - directing said florescence scattering return signals to a florescence channel imager; and
   - ascertaining the presence of a sea object based on images from at least one of said LIDAR imager, said Raman channel imager and florescence channel imager.

14. The method of claim 13, wherein said directing said Rayleigh scattering return signals further includes directing and Rayleigh scattering return signals to said LIDAR channel imager via a long-pass beam splitter.

15. The method of claim 13, wherein directing said Raman scattering return signals and said florescence scattering return signals further includes directing said Raman scattering return signals to said Raman channel imager and directing said florescence scattering return signals to said florescence channel imager via a short-pass beam splitter.

16. The method of claim 13, wherein said ascertaining further includes ascertaining the presence of a sea mine based on presence and absence of spots on said images.

\* \* \* \* \*